United States Patent [19]

Theopold et al.

[11] Patent Number: 4,902,486

[45] Date of Patent: Feb. 20, 1990

[54] NOVEL GALLIUM ARSENIDE PRECURSOR AND LOW TEMPERATURE METHOD OF PREPARING GALLIUM ARSENIDE THEREFROM

[75] Inventors: Klaus H. Theopold, Ithaca, N.Y.; Erin K. Byrne, Bridgewater, N.J.

[73] Assignee: Cornell Research Foundation, Inc., Ithaca, N.Y.

[21] Appl. No.: 307,995

[22] Filed: Feb. 9, 1989

Related U.S. Application Data

[63] Continuation-in-part of Ser. No. 116,212, Nov. 3, 1987.

[51] Int. Cl.$^4$ ............................................. C01F 15/00
[52] U.S. Cl. ............................ 423/122; 252/62.3 GA; 420/555
[58] Field of Search ............... 252/62.3 GA; 420/555, 420/579; 148/52; 423/112, 122

[56] References Cited

U.S. PATENT DOCUMENTS

| | | | |
|---|---|---|---|
| 2,964,550 | 12/1960 | Seyferth | 556/12 |
| 3,226,270 | 12/1965 | Miederer | 437/110 |
| 3,414,597 | 12/1968 | Wickus | 556/11 |
| 3,763,197 | 10/1973 | Collier | 556/12 |
| 3,969,386 | 7/1976 | Ballard et al. | 556/11 |
| 4,399,097 | 8/1983 | Gallagher et al. | 420/555 |
| 4,427,714 | 1/1984 | Davey | 437/81 |
| 4,798,701 | 1/1989 | David | 420/555 X |

OTHER PUBLICATIONS

CA 109(20): 182366y (1988).

Primary Examiner—Patrick P. Garvin
Assistant Examiner—George R. Fourson

[57] ABSTRACT

A novel gallium arsenide precursor has the formula $R_2GaAs(SiR')_2$ wherein R is selected from the group consisting of alkyl substituted cycloaliphatic group and alkyl substituted aromatic group and R' is alkyl. Preferably, R is pentamethylcyclopentadienyl and R' is methyl. The precursor is reacted with an alcohol, preferably ethanol or t-butanol at a temperature ranging from $-20°$ to $60°$ C., preferably at room temperature, under water free conditions to form solid gallium arsenide and byproducts which are liquid under the reaction conditions. The gallium arsenide forming reaction may be aided by a catalyst providing amount of a substance which is considered to react with excess alcohol reactant to generate a catalytic amount of HCl, e.g., $(CH_3)_3SiCl$ or $[R(Cl)GaAs(SiR'_3)_2]_n$ wherein R is pentamethylcyclopentadienyl and R' is methyl and in solution in benzene n is 1 and 3.

8 Claims, No Drawings

NOVEL GALLIUM ARSENIDE PRECURSOR AND LOW TEMPERATURE METHOD OF PREPARING GALLIUM ARSENIDE THEREFROM

This invention was made with the Government support under Grant No. CHE 8451670, awarded by National Science Foundation. The Government has certain rights in the invention.

CROSS-REFERENCE TO RELATED APPLICATION

This is a continuation-in-part of U.S. Ser. No. 116,212, filed Nov. 3, 1987, now allowed.

TECHNICAL FIELD

This invention is directed to novel arsinogallane compounds and to a method of preparing gallium arsenide therefrom.

BACKGROUND OF THE INVENTION

The common method for synthesizing gallium arsenide is known as the metal organic chemical vapor deposition (MOCVD) method and involves passing gaseous trimethyl gallium and a large excess of gaseous arsine down a tube to deposit gallium arsenide on a heated substrate. This method has the disadvantage of relying on large quantities of a very toxic gas, arsine, and very high reaction temperatures, namely 600° C. to 700° C.

Another method for forming gallium arsenide is disclosed in Gallagher et al U.S. Pat. No. 4,399,097 wherein a complex having the formula $Ga_a(NH_4)_bH_c(AsO_4)_y$ is reduced in a hydrogen atmosphere at an elevated temperature, typically in the range of 400° to 900° C. While this method avoids use of toxic arsenic containing reactants in gaseous form since the complex is prepared utilizing arsenic pentoxide, it also has the disadvantage of requiring very high reaction temperatures.

Jensen U.S. Pat. No. 4,594,264 discloses forming gallium arsenide by applying a liquid film of gallium arsenic complex of the formula $X_3GaAsR_3$ in solvent, evaporating the solvent and irradiating. This method has the disadvantage of requiring an evaporation step after complex is isolated and requires irradiating (A laser is the only means for irradiating which is specifically named).

SUMMARY OF THE INVENTION

It has been found herein that novel gallium arsenide precursors can be prepared and converted into gallium arsenide without use of gaseous arsenic-containing compounds, high temperatures, an evaporation step after precursor isolation or irradiation.

The novel gallium arsenide precursor herein is arsinogallane compound having the formula $R_2GaAs(SiR'_3)_2$ wherein R is selected from the group consisting of cycloaliphatic group, alkyl substituted cycloaliphatic group and alkyl substituted aromatic group, and R' is alkyl.

To form gallium arsenide, the precursor is reacted with alcohol present in excess and having the formula $R''(OH)_x$ wherein R'' is alkyl containing from 1 to 10 carbon atoms and x ranges from 1 to 3, at a temperature ranging from −20° C. to 60° C. under water free conditions. The gallium arsenide is formed as a solid which precipitates under reaction conditions while the by-products are liquid or dissolved under the reaction conditions so that the gallium arsenide is readily recovered.

DETAILED DESCRIPTION

We turn now in detail to the gallium arsenide precursor having the formula $R_2GaAs(SiR'_3)_2$.

In said formula, cycloaliphatic group or moiety of R can be, for example, cyclobutyl, cyclopentyl, cyclohexyl, cycloheptyl, cyclooctyl, cyclononyl, norbornyl,2,2,2-bicyclooctyl, cyclobutenyl, cyclopentenyl, cyclopentadienyl, cyclohexenyl, cyclohexadienyl, norbornyl, cycloheptenyl, cycloheptatrienyl, cyclooctadienyl and cyclopentadecenyl.

In said formula, aromatic moiety of R can be, for example, phenyl or indenyl.

In said formula, alkyl substituent of R can be one or a plurality of the same or different straight chain or branched chain alkyl groups. Preferably each said alkyl substituent contains from 1 to 5 carbon atoms. Very preferred alkyl substituent of R comprises a plurality of methyl groups.

In said formula, preferred R groups include, for example, pentamethylcyclopentadienyl, mesityl and 1-norbornyl.

In said formula, R' preferably contains from 1 to 5 carbon atoms and can be straight chain or branched chain. Very preferably R' is methyl.

The precursor $R_2GaAs(SiR'_3)_2$ is readily prepared by reacting $(R_2GaCl)_2$ with $LiAs(SiR'_3)_2$ wherein R and R' are defined as above. This reaction is readily carried out utilizing stoichiometric amounts of the reactants at a temperature ranging from −20° C. to 60° C. in a solvent which can be aliphatic hydrocarbon, aromatic hydrocarbon or ether solvent. Substantial completeness of reaction is obtained over a period of about 2 hours at −20° C. to less than a minute at 60° C. Preferably, this reaction is carried out at room temperature, e.g, 26° C. to 28° C., and substantial completeness of reaction is normally obtained in 2 to 10 minutes. Suitable solvents include, for example, pentane, cyclopentane, hexane, cyclohexane, methylcyclohexane, heptane, benzene, toluene, xylene, tetrahydrofuran, dimethyltetrahydrofuran, diethyl ether, dimethoxyethane, and dioxane. Preferred solvents are benzene and pentane. The reaction should be carried out in the absence of water since water reacts with the starting materials and formed precursor. In the reaction the formed precursor $R_2GaAs(SiR'_3)_2$ remains dissolved in the reaction solvent and by-product lithium chloride, precipitates. Precursor $R_2GaAs(SiR'_3)_2$ is readily obtained in substantially purified form by removing the resulting solution from the precipitated lithium chloride by-product, for example, by filtering, stripping solvent from $R_2GaAs(SiR'_3)_2$ product, for example, at room temperature under vacuum and recrystallizing from hydrocarbon solvent, e.g. pentane at −35° C. The reaction is preferably carried out under an inert atmosphere, e.g., under dry nitrogen, to preclude the presence of moisture.

The starting material $(R_2GaCl)_2$ is readily made by the method described in Beachley et al, Organomet. 4, 1675 (1985).

The starting material $LiAs(SiR'_3)_2$ is readily prepared by reacting arsenic with 1.90 equivalents of sodium and 1.56 equivalents of potassium in dimethoxyethane, e.g., at reflux temperature for 36 hours, and then reacting at reflux temperature with $ClSiR'_3$ thereby to form $As(SiR'_3)_3$ and reacting this product with methyllithium in tetrahydrofuran. The preparation of $LiAs(SiMe_3)_2$ where Me is methyl is described in Becker, G., et al, Z. Anorg. Allg. Chem, 462, 113 (1980).

A preferred arsinogallane (gallium arsenide precursor) has the formula $R_2GaAs(SiR'_3)_2$ wherein R is pentamethylcyclopentadienyl and R' is methyl. This compound is a yellow crystalline solid having a melting point of 112° C.-118° C. and a vapor pressure below $1.75 \times 10^{-5}$ torr. at 298° K. (so it does not easily vaporize and is easily handled without danger). It reacts immediately with water and slowly with oxygen.

We turn now to the reaction whereby the precursor $R_2GaAs(SiR'_3)_2$ is converted to gallium arsenide.

The reaction proceeds to produce gallium arsenide as product which precipitates from the reaction solution and RH and $R''OSiR'_3$ as by-products (R,R' and R'' are defined as above) which are liquid and/or soluble in the reaction solution.

The alcohol reactant $R''(OH)_x$ for this conversion reaction can be straight chain or branched. Suitable alcohols include, for example, ethanol, propanol, iso-propanol, n-butanol, s-butanol, t-butanol, ethylene glycol, pinacol, glycerin, and phenol. Preferred alcohol reactants are ethanol and t-butanol. Since the reaction to form gallium arsenide is conducted in the absence of water, absolute alcohols should be used as reactants.

Preferably this reaction to convert precursor to gallium arsenide is carried out at room temperature; e.g. 26° C.-28° C.

The reaction to convert precursor to gallium arsenide is carried out to substantial completeness in several, e.g., 12 hours at −20° C. to less than a minute, e.g., in 30 seconds, at 60° C. At room temperature the reaction is carried out to substantial completeness in a period of about 1 minute to about 1 hour with shorter times being a function of the amount of excess of the alcohol reactant and the concentration of the alcohol reactant in the reaction solution; a reaction time of up to 12 hours or more can be useful when the alcohol reactant is used in a stoichiometric amount.

Preferably the alcohol reactant is present in an amount of 2 to 100 equivalents per equivalent of arsinogallane (precursor) reactant.

The reaction to convert precursor to gallium arsenide is readily carried out in a solvent selected from the group consisting of aliphatic, aromatic and ether solvents. Very suitable solvents include pentane, cyclopentane, hexane, cyclohexane, methylcyclohexane, heptane, benzene, toluene, xylene, trahydrofuran, dimethyl-tetrahydrofuran, diethyl ether, dimethoxyethane, and dioxane. Toluene, benzene and pentane are preferred solvents. The reaction solvent is selected so that gallium arsenide product precipitates from the reaction solution and so that by-product RH and $R''OSiR'_3$ are liquids under the reaction conditions or dissolved in the reaction solvent. Protic and halogenated solvents should not be used.

The reaction to convert precursor to gallium arsenide is preferably carried out under an inert atmosphere, e.g., under dry nitrogen, to preclude to presence of moisture.

The reaction to convert precursor to gallium arsenide is aided by a catalyst providing amount of a substance which is present with the precursor as an impurity and/or which is added which is considered to react with excess $R''(OH)_x$ to generate a catalytic amount of HCl.

One catalyst providing substance is $(CH_3)_3SiCl$ used in an amount, for example, ranging 1/10 to ½ mole per mole of precursor. Addition in amount of about ⅓ mole per mole of precursor has been found to speed the reaction by a factor of about 3.

Another catalyst providing substance is obtained by reacting $R_2GaAs(SiR'_3)_2$ wherein R is pentamethylcyclopentadienyl and R' is methyl with 1 equivalent of HCl at room temperature and has been assigned the composition $[R(Cl)GaAs(SiR'_3)_2]_n$ and wherein R is pentamethylcyclopentadienyl and R' is methyl and wherein in solution in benzene n is 1 and 3 so that there is present approximately equal weights of monomer and trimer. This (both the monomer and trimer components) reacts instantaneously with t-butanol to yield gallium arsenide and thus in addition to providing a catalyst provides product. This is used, for example, in an amount ranging from about 1/50 mole to about ½ mole per mole of precursor. Use in an amount of about 1/10 mole per mole of precursor has been found to speed the reaction by a factor of about 10. Both said monomer and said trimer as well as the combination thereof are considered to have catalyst providing effect.

The formed gallium arsenide, as indicated above, is the only reaction product to precipitate from solution and is readily recovered by separating the precipitate from the reaction solution, e.g. by filtering or evaporating solvent and by-products. The gallium arsenide product is recovered as a substantially pure reddish-brown, amorphous powder by washing, e.g. with solvent for by-products, preferably pentane or toluene followed by tetrahydrofuran and then heating under vacuum at, for example, 100° C. to remove residual solvent.

The amorphous gallium arsenide product may be used in solar cells, or the amorphous product can be converted to crystalline form by methods known in the art, e.g., by annealing at a temperature ranging from 200° C. to 1238° (m.p.). The crystalline material is useful for semiconductors.

Instead of recovering precipitated gallium arsenide in amorphous form, the reaction of the precursor with alcohol can be carried out in the presence of crystalline gallium arsenide substrate to deposit formed gallium arsenide epitaxially on said substrate.

The invention is illustrated by the following specific example:

EXAMPLE $LiAs(SiMe_3)_2$ wherein Me stands for methyl was prepared by the method of Becker, G., et al, Z. Anorg. Allg. Chem., 462, 113 (1980).

$(R_2GaCl)_2$ wherein R is pentamethylcyclopentadienyl was prepared by the method by Beachley et al, Organomet., 4, 1675 (1985).

Approximately 16 ml of pentane was introduced into a vial under nitrogen in a drybox. Into the vial were then added first 0.608 mmole of the $(R_2GaCl)_2$ and then 0.608 mmole of the $LiAs(SiMe_3)_2$. The reaction mix was then stirred at room temperature for 1 hour to ensure completion of reaction. Then a white precipitate was removed by filtration. The filtrate was stripped of solvent under vacuum, to yield a yellow solid. This material was recrystallized from pentane at −35° C. to yield 0.10gm of yellow plates of substantially pure crystalline compound; $R_2GaAs(SiR'_3)_2$ wherein R is pentamethylcyclopentadienyl and R' is methyl. The structure was confirmed by NMR, elemental analysis (calculated: %C=55.62; %H=8.62; Found: %C=55.95; %H=8.79), infrared, and molecular weight determination. Yield obtained was 63% of theoretical. The product was a crystalline solid with a vapor pressure less than $1.75 \times 10^{-5}$ torr. at 298° K. It dissolved readily in pentane, benzene, and tetrahydrofuran solvents. The melting point of the product was 112° C. to 118° C.

Product made as above was converted to gallium arsenide as follows:

Approximately 12 ml of pentane was introduced into a flask with sidearm under nitrogen in a drybox. Into the flask was added 0.863 mmole $R_2GaAs(SiR'_3)_2$ where R is pentamethylcyclopentadienyl and R' is methyl, and the flask was capped with a septum. The flask was taken out of the drybox and attached to a nitrogen bubbler through the sidearm. Two equivalents (1.726 mmoles) of tert-butanol was added via syringe through the septum. The reaction mixture was stirred at room temperature for 12 hours; then the flask was evacuated and brought back into drybox. At this point, the mixture appeared reddish-brown in color and a reddish-brown precipitate was evident. In the drybox the solvent was evaporated to yield 0.108 g reddish-brown solid. The solid was washed with toluene and then tetrahydrofuran and dried under the vacuum. The product was confirmed by analysis to be substantially pure gallium arsenide.

The gallium arsenide obtained was a reddish brown, amorphous (by X-ray diffraction) powder.

When in the above gallium arsenide preparation, 0.3 moles of $(CH_3)_3SiCl$ is added to the reaction mixture, reaction is completed in about 4 hours.

When in the above gallium arsenide preparation there is added 0.1 mole of $[R(Cl)GaAs(SiR'_2)_2]_n$ as described above, reaction is completed in 1 to 1½ hours. $[R(Cl)GaAs(SiR'_2)]_n$ as described above was prepared as follows: In a drybox, a 100 ml flask was charged with precursor $R_2GaAs(SiR'_3)_2$ wherein R is pentamethylcyclopentadienyl and R' is methyl (0.545 g, 0.972 mmoles), 21 ml $C_5H_{12}$, and a stir bar. A needle valve was attached and the system degassed on the high vacuum line. One equivalent HCl (275 torr, 25° C., 67 ml, 0.972 mmoles) was condensed into the flask. Upon thawing, the solution color was yellow and a red precipitate was evident. After three days at room temperature, the solution color was yellow-orange and a small amount of precipitate was still present. The solvent was evaporated and the system returned to the drybox. The solid products were extracted with $C_5H_{12}$, which was then evaporated. The resulting orange solid was recrystallized at $-30°$ C. from $C_5H_{12}$. Orange crystals were isolated (0.103g), which were again recrystallized to yield 0.030g (0.065 mmoles, 7%) colorless crystals. $^1H$ NMR ($C_6D_6$): δ 1.96(s,45H), 0.56 (s,54H), 1.94(s,15H), 0.36(s,18H). The former two resonances correspond to the trimeric form, the latter two to the monomeric. Anal.: Calc'd. for $C_{16}H_{33}AsClGaSi_2$: C, 41.62; H, 7.20; Cl, 7.68. Found: C, 41.44; H, 7.16; Cl, 7.85.

$R_2GaAs(SiR'_3)_2$ wherein R is mesityl and R' is methyl is obtained by substituting an equivalent amount of $(R_2GaCl)_2$ wherein R is mesityl for the $(R_2GaCl)_2$ above where R is pentamethylcyclopentadienyl.

$R_2GaAs(SiR'_3)$ wherein R is 1-norbornyl and R' is methyl is obtained by substituting an equivalent amount of $(R_2GaCl)_2$ wherein R is 1-norbornyl for the $(R_2GaCl)_2$ above where R is pentamethylcyclopentadienyl.

The precursors described above where R is mesityl and where R is 1-norbornyl are readily converted to gallium arsenide by substituting an equivalent amount of each for the precursor where R is pentamethylcyclopentadienyl in the reaction with t-butanol described above.

The reactions convert $R_2GaAs(SiR'_3)_2$ to gallium arsenide described above produce substantially equivalent results when an equivalent amount of absolute ethanol is substituted for the t-butanol.

The reactions to convert $R_2GaAs(SiR'_3)_2$ to gallium arsenide described above produce substantially equivalent results when the same volume of toluene or benzene is substituted for the pentane.

Other variations will be evident to those skilled in the art. Therefore, the scope of the invention is intended to be defined by the claims.

What is claimed is:

1. Process for preparing gallium arsenide comprising the steps of reacting an arsinogallane with an alcohol which is present in stoichiometric excess and has the formula $R''(OH)_x$ wherein $R''$ is alkyl containing from 1 to 10 carbon atoms and x ranges from 1 to 3, at a temperature ranging from $-20°$ C. to 60° C. under water free conditions to form solid gallium arsenide which precipitates and by-products which are liquid or dissolved under the reaction conditions, said arsinogallane having the formula $R_2GaAs(SiR'_3)_2$ wherein R is selected from the group consisting of cycloaliphatic group, alkyl substituted cycloaliphatic group and alkyl substituted aromatic group and R' is alkyl.

2. Process as recited in claim 1 wherein the arsinogallane reactant has the formula $R_2GaAs(SiR'_3)_2$ wherein R is pentamethylclopentadienyl and R' is methyl and wherein said alcohol is selected from the group consisting of ethyl alcohol and t-butyl alcohol.

3. Process as recited in claim 2 wherein the reaction is carried out at room temperature in a solvent selected from the group consisting of aliphatic, aromatic and ether solvents wherein the alcohol reactant is present in an amount of 2 to 100 equivalents per equivalent of arsinogallane reactant.

4. Process as recited in claim 3 wherein there is included a catalyst providing amount of a substance which reacts with the excess alcohol reactant to generate a catalytic ally effective amount of HCl.

5. Process as recited in claim 3 wherein there is included a catalyst providing amount of $(CH_3)_3SiCl$.

6. Process as recited in claim 3 wherein there is included a catalyst providing amount of at least one substance selected from the group consisting of monomeric and trimeric forms of $R(Cl)GaAs(SiR'_3)_2$ wherein R is pentamethylcyclopentadienyl and R' is methyl.

7. The process of claim 1 wherein the arsinogallane reacted is the essential component of a composition prepared by a process comprising reacting LiAs(-SiMe$_3$)$_2$ where Me is methyl and $(R_2GaCl)_2$ where R is pentamethylcyclopentadienyl in the absence of water in stoichiometric amounts at room temperature in aliphatic hydrocarbon solvent to obtain substantial completeness of reaction to provide a solution where reaction product is dissolved in said solvent and a by-product precipitate, separating the solution from the precipitate, removing a solvent form the solution to obtain a solid and recrystallizing said solid thereby to obtain said composition.

8. The process of claim 7 where said aliphatic solvent is pentane and said recrystallizing is from pentane.

* * * * *

UNITED STATES PATENT AND TRADEMARK OFFICE
CERTIFICATE OF CORRECTION

PATENT NO. : 4,902,486

DATED : February 20, 1990

INVENTOR(S) : Klaus H. Theopold

It is certified that error appears in the above-identified patent and that said Letters Patent is hereby corrected as shown below:

Claim 4 (column 6, line 43), "catalytic ally" should be --catalytically--.

Claim 7 (column 6, line 61), "a solvent form" should be --solvent from--.

Signed and Sealed this

Twenty-ninth Day of October, 1991

*Attest:*

HARRY F. MANBECK, JR.

*Attesting Officer*     *Commissioner of Patents and Trademarks*